United States Patent
O'Mahony et al.

(10) Patent No.: US 8,722,073 B2
(45) Date of Patent: May 13, 2014

(54) POST IRRADIATION SHELF-STABLE DUAL PASTE DIRECT INJECTABLE BONE CEMENT PRECURSOR SYSTEMS AND METHODS OF MAKING SAME

(71) Applicant: Howmedica Osteonics Corp., Mahwah, NJ (US)

(72) Inventors: Donal O'Mahony, Limerick (IE); Venkat R. Garigapati, Southborough, MA (US); Adrian Sun Wai, Limerick (IE); Brian Hess, Charlestown, MA (US); Matthew E. Murphy, Pembrokestown (IE)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 13/911,721

(22) Filed: Jun. 6, 2013

(65) Prior Publication Data
US 2013/0264244 A1    Oct. 10, 2013

Related U.S. Application Data

(63) Continuation of application No. 12/970,393, filed on Dec. 16, 2010, now Pat. No. 8,481,065.

(60) Provisional application No. 61/287,793, filed on Dec. 18, 2009.

(51) Int. Cl.
| A61F 2/00 | (2006.01) |
| A61F 2/28 | (2006.01) |
| A61L 24/00 | (2006.01) |
| A61L 24/02 | (2006.01) |
| A61L 24/04 | (2006.01) |

(52) U.S. Cl.
USPC ........... 424/422; 424/423; 424/426; 424/602; 623/16.11; 623/23.56; 623/23.58; 623/23.62

(58) Field of Classification Search
USPC .................................. 424/422, 423, 426, 602
See application file for complete search history.

(56) References Cited

U.S. PATENT DOCUMENTS

| 4,772,468 A | 9/1988 | Pfirrmann |
| 4,843,112 A | 6/1989 | Gerhart et al. |

(Continued)

FOREIGN PATENT DOCUMENTS

| EP | 1712245 A2 | 10/2006 |
| JP | 2006130122 A | 5/2006 |

(Continued)

OTHER PUBLICATIONS

Abstract of: Desai et al. Drug Deliv. 2006, 13(1), 39-50) 1 page.

(Continued)

*Primary Examiner* — Ernst Arnold
(74) *Attorney, Agent, or Firm* — Lerner, David, Littenberg, Krumholz & Mentlik, LLP

(57) ABSTRACT

The present invention relates to a bone cement precursor system that is presented in the form of two shelf-stable pastes which have been terminally sterilized and are held in separate containers during product transport and storage. When the product is used during surgery, these pastes inject to a site of application through a static mixing device by the action of applied injection force. When the two pastes are mixed, they start to react to each other while injecting out. The resulting composition is highly biocompatible, osteoconductive, injectable, rapid setting and bioresorbable, and is useful in connection with bone repair procedures, for example, in the craniomaxillofacial, trauma and orthopedic areas.

27 Claims, 3 Drawing Sheets

(56) References Cited

U.S. PATENT DOCUMENTS

| | | | |
|---|---|---|---|
| 4,861,733 A | 8/1989 | White | |
| 4,869,906 A | 9/1989 | Dingeldein et al. | |
| 4,880,610 A | 11/1989 | Constantz | |
| 5,047,031 A | 9/1991 | Constantz | |
| 5,053,212 A | 10/1991 | Constantz et al. | |
| 5,129,905 A | 7/1992 | Constantz | |
| 5,137,534 A | 8/1992 | Sumita | |
| 5,178,845 A | 1/1993 | Constantz et al. | |
| 5,262,166 A | 11/1993 | Liu et al. | |
| 5,336,264 A | 8/1994 | Constanz et al. | |
| 5,434,440 A | 7/1995 | Yoshitomi et al. | |
| 5,522,893 A | 6/1996 | Chow et al. | |
| 5,525,148 A | 6/1996 | Chow et al. | |
| 5,542,973 A | 8/1996 | Chow et al. | |
| 5,545,254 A | 8/1996 | Chow et al. | |
| 5,569,442 A | 10/1996 | Fulmer et al. | |
| 5,683,496 A | 11/1997 | Ison et al. | |
| 5,695,729 A | 12/1997 | Chow et al. | |
| 5,697,981 A | 12/1997 | Ison et al. | |
| 5,709,742 A | 1/1998 | Fulmer et al. | |
| 5,782,971 A | 7/1998 | Constantz et al. | |
| 5,797,873 A | 8/1998 | Franz et al. | |
| 5,820,632 A | 10/1998 | Constantz et al. | |
| 5,846,312 A | 12/1998 | Ison et al. | |
| 5,900,254 A | 5/1999 | Constantz | |
| 5,952,010 A | 9/1999 | Constantz | |
| 5,954,867 A | 9/1999 | Chow et al. | |
| 5,962,028 A | 10/1999 | Constantz | |
| 5,968,253 A | 10/1999 | Poser et al. | |
| 5,968,999 A | 10/1999 | Ramp et al. | |
| 6,002,065 A | 12/1999 | Constantz et al. | |
| 6,005,162 A | 12/1999 | Constantz | |
| 6,030,635 A | 2/2000 | Gertzman et al. | |
| 6,201,039 B1 | 3/2001 | Brown et al. | |
| 6,235,665 B1 | 5/2001 | Pickrell et al. | |
| 6,277,151 B1 | 8/2001 | Lee et al. | |
| 6,318,841 B1 | 11/2001 | Coleman et al. | |
| 6,325,992 B1 | 12/2001 | Chow et al. | |
| 6,340,648 B1 | 1/2002 | Imura et al. | |
| 6,409,972 B1 | 6/2002 | Chan | |
| 6,485,754 B1 | 11/2002 | Wenz et al. | |
| 6,491,900 B2 | 12/2002 | Chow et al. | |
| 6,511,510 B1 | 1/2003 | de Bruijn et al. | |
| 6,521,246 B2 | 2/2003 | Sapieszko et al. | |
| 6,547,866 B1 | 4/2003 | Edwards et al. | |
| 6,585,992 B2 | 7/2003 | Pugh et al. | |
| 6,616,742 B2 | 9/2003 | Lin et al. | |
| 6,642,285 B1 | 11/2003 | Bohner | |
| 6,648,960 B1 | 11/2003 | Lin et al. | |
| 6,706,690 B2 | 3/2004 | Reich et al. | |
| 6,713,420 B2 | 3/2004 | Imura et al. | |
| 6,793,725 B2 | 9/2004 | Chow et al. | |
| 6,800,360 B2 | 10/2004 | Miyanaga et al. | |
| 6,821,916 B2 | 11/2004 | Myoi et al. | |
| 6,929,692 B2 | 8/2005 | Tas | |
| 6,955,716 B2 | 10/2005 | Xu et al. | |
| 6,979,700 B2 | 12/2005 | Ma | |
| 6,994,726 B2 | 2/2006 | Lin et al. | |
| 7,018,460 B2 | 3/2006 | Xu et al. | |
| 7,118,705 B2 | 10/2006 | Lin et al. | |
| 7,151,120 B2 | 12/2006 | Ma | |
| 7,163,651 B2 | 1/2007 | Chern Lin et al. | |
| 7,258,734 B2 | 8/2007 | Lin et al. | |
| 7,294,187 B2 | 11/2007 | Chow et al. | |
| 7,318,841 B2 | 1/2008 | Tofighi et al. | |
| 7,326,426 B2 | 2/2008 | Nathan et al. | |
| 7,351,280 B2 | 4/2008 | Khairoun et al. | |
| 7,407,542 B2 | 8/2008 | Lemaitre et al. | |
| 7,473,312 B2 | 1/2009 | Barralet et al. | |
| 7,709,029 B2 | 5/2010 | Chow et al. | |
| 7,892,346 B2 | 2/2011 | Insley et al. | |
| 8,557,038 B2 | 10/2013 | Chow et al. | |
| 2002/0120351 A1 | 8/2002 | Tuomela et al. | |
| 2003/0078317 A1 | 4/2003 | Lin et al. | |
| 2003/0152606 A1 | 8/2003 | Gerber | |
| 2004/0048947 A1 | 3/2004 | Lidgren et al. | |
| 2004/0137032 A1 | 7/2004 | Wang | |
| 2004/0141903 A1 | 7/2004 | Zitelli et al. | |
| 2004/0151751 A1 | 8/2004 | Cooper | |
| 2004/0266943 A1 | 12/2004 | Oriakhi | |
| 2005/0029701 A1 | 2/2005 | Lin et al. | |
| 2005/0074415 A1 | 4/2005 | Chow et al. | |
| 2005/0087903 A1 | 4/2005 | Farr et al. | |
| 2005/0119746 A1 | 6/2005 | Lidgren | |
| 2005/0184417 A1 | 8/2005 | Chern Lin et al. | |
| 2005/0230870 A1 | 10/2005 | Oriakhi | |
| 2005/0267592 A1 | 12/2005 | Lin et al. | |
| 2005/0271740 A1 | 12/2005 | Lin et al. | |
| 2005/0271741 A1 | 12/2005 | Lin et al. | |
| 2005/0271742 A1 | 12/2005 | Chern Lin et al. | |
| 2006/0205652 A1 | 9/2006 | Zamora et al. | |
| 2006/0225620 A1 | 10/2006 | Murphy et al. | |
| 2006/0263443 A1 | 11/2006 | Chow et al. | |
| 2007/0041906 A1 | 2/2007 | Lidgren et al. | |
| 2007/0092580 A1 | 4/2007 | Chow et al. | |
| 2007/0092856 A1 | 4/2007 | Chow et al. | |
| 2007/0186818 A1 | 8/2007 | Bohner | |
| 2007/0218144 A1 | 9/2007 | Lally | |
| 2007/0260325 A1 | 11/2007 | Wenz | |
| 2007/0282455 A1 | 12/2007 | Luginbuehl et al. | |
| 2007/0283849 A1 | 12/2007 | Edidin et al. | |
| 2008/0014242 A1 | 1/2008 | Overby et al. | |
| 2008/0153784 A1 | 6/2008 | Zhang et al. | |
| 2008/0194810 A1 | 8/2008 | Kim et al. | |
| 2008/0206716 A1 | 8/2008 | Asgary | |
| 2008/0208354 A1 | 8/2008 | Bohner et al. | |
| 2009/0048145 A1 | 2/2009 | Hellerbrand et al. | |
| 2009/0054545 A1 | 2/2009 | Muratoglu et al. | |

FOREIGN PATENT DOCUMENTS

| | | |
|---|---|---|
| JP | 2006289092 A | 10/2006 |
| JP | 2009512517 A | 3/2009 |
| JP | 2009512713 A | 3/2009 |
| JP | 2009082913 A | 4/2009 |
| WO | 2005117919 A2 | 12/2005 |

OTHER PUBLICATIONS

International Search Report, PCT/US2010/060793, dated Apr. 18, 2011.

Japanese Office Action for Application No. 2012-508835 dated Apr. 20, 2012.

Wach et al. (nuclear instruments and Methods in Physics Research B 2003 211, 533-544.

K. Ishikawa et al., Properties and Mechanisms of Fast-Setting Calcium Phosphate Cements, Journal of Materials Science: Materials in Medicine , Sep. 1995, vol. 6, Issue 9, pp. 528-533.

POST IRRADIATION SHELF-STABLE DUAL PASTE DIRECT INJECTABLE BONE CEMENT PRECURSOR SYSTEMS AND METHODS OF MAKING SAME

CROSS-REFERENCE TO RELATED APPLICATIONS

The present application is a continuation of U.S. patent application Ser. No. 12/970,393, filed Dec. 16, 2010, which is now U.S. Pat. No. 8,481,065, and which claims benefit of the filing date of U.S. Provisional Patent Application No. 61/287,793, filed Dec. 18, 2009, the disclosure of which is incorporated herein by reference.

FIELD OF THE INVENTION

The field of this invention pertains to a bone cement for bone filler applications and in the preparation of such cement. More specifically, the invention relates a post irradiation shelf-stable dual paste direct injectable bone cement precursor systems suitable for implanting within the human body and methods of making same.

BACKGROUND OF THE INVENTION

Calcium phosphate based cements (CaPC) have been used as bone substitutes and bone grafts for nearly twenty years. In the 1980s, the research was focused on developing a formulation that was biocompatible for the intended use of clinical applications. These CaPC formulations have historically been provided in the form of a powder and liquid system, which upon mixing becomes a paste and goes through a partial dissolution that initiates a precipitation reaction resulting in the setting of the cement. Often such cements are based on an acid-base reaction to form a salt which usually takes the form of the calcium phosphate phase identified as hydroxyapatite or brushite.

Most of the presently available calcium phosphate precursor cement formulations are still a powder/liquid system wherein the powder and the liquid components are separately packaged and only to be combined prior to use at time of surgery. The mixing is accomplished by either (a) manual mixing, or (b) use of a mechanical based mixing system provided in a commercial product. However, both approaches have some shortcomings. The manual system is sometimes perceived to be time consuming, and user dependent/sensitive. The custom designed mechanical systems aim to provide a more satisfactory user experience by providing consistency and reproducibility for the end user, but are still considered to be cumbersome, difficult to use and cost ineffective.

Accordingly, there have been studies reported with the aim to develop premixed, self-hardening, cement pastes. For example, U.S. Pat. No. 6,793,725 describes a self-hardening calcium phosphate based bone cement paste that is mixed with liquid glycerol, hydroxypropyl methylcellulose and sodium phosphate. This premixed paste formulation allegedly remains stable over a period of time and hardens only when delivered to a desired site in a human body. This premixed paste formulation, however, does not exhibit a good washout resistance when it is applied to an open wet field in a human body, and is therefore limited in utility.

U.S. Patent Publication No. 2006/0263443 also discloses a premixed self-hardening calcium phosphate based bone cement paste containing a gelling agent, such as hydroxymethyl cellulose, carboxymethyl cellulose, chitosan, collagen, gum, gelatin and alginate, to enhance paste cohesiveness and washout resistance. This type of cement, allegedly possesses excellent physical properties, but it is also limited in utility since cement hardening in the interior of the cement mass is slow under some clinical bone grafting conditions, for instance, wherein the amount of water available from the tissue is limited, or wherein the interior of the cement is more than several millimeters away from the nearest graft-tissue interface.

U.S. Patent Publication No. 2007/0092580 teaches a self-setting dual phase cement precursor system composed of a first and second discrete containers, at least one of which is aqueous. The cement formed by combining these two phases, however, do not have a long-term shelf life, as the phases in each of these two pastes packaged in separate containers tend to destabilize/separate during storage. This is especially true after the dual paste system is sterilized using gamma radiation. Therefore, this formulation also is limited in utility.

The present invention aims at responding to the currently unanswered user need for providing a premixed dual paste injectable bone cement precursor system that is shelf stable even after it is sterilized using gamma radiation for in vivo usage, and that rapidly sets as a biocompatible bone cement possessing excellent physical properties when combined.

SUMMARY OF THE INVENTION

In one aspect of the invention, the invention relates to a rapid setting bone cement precursor system that is presented in the form of two shelf-stable pastes that are held in separate containers during product transport and storage. When the product is used during surgery, these pastes inject to a site of application through a specially designed static mixing device by the action of applied injection force. When the two pastes are mixed, they start to react to each other while injecting out. The reaction is continued at the site of application in the body environment, wherein the mixture of pastes converts into a bone cement in a specified time. The resulting cement is highly biocompatible, osteoconductive, injectable and bioresorbable that is useful in connection with bone repair procedures, for example, in the craniomaxillofacial, trauma and orthopedic areas.

In another aspect of the invention, the at least two pastes containing bone cement precursors are shelf stable even after terminal sterilization, e.g. using gamma irradiation, for in vivo use.

In yet another aspect of the invention, the invention provides a post irradiation shelf-stable product with greater than 3 month, preferably 6 month, and most preferably greater than 1 year of shelf life.

It is also an aspect of the invention to provide a stable and injectable bone cement precursor system comprising an acidic aqueous paste and an alkaline non-aqueous paste. The pastes themselves are not cements, but they may be combined to form a biocompatible bone cement that is useful in connection with bone repair procedure.

In a preferred embodiment, the acidic aqueous paste and the alkaline non-aqueous paste are designed to withstand terminal sterilization, such as gamma radiation, and still meet the long-term shelf life stability and injectability when kept separate, and reactivity to each other when mixed to set and form hydroxyapatite-based bone cement in a specified time. The resulting bone cement has superior biocompatibility and mechanical properties exhibiting excellent wet field wash out resistant properties.

Terminal sterilization, such as gamma irradiation, and pH have dramatic effect on the structural stability of polymer additives which may be used in these two pastes as they are either degraded into low molecular weight species or cross linked into polymeric gels which alters the viscosity. Accordingly, in order to provide a post irradiation shelf-stable bone cement precursor system, the polymer additives in accordance with an aspect of the present invention must be able to survive the terminal sterilization and extreme pH conditions.

Applicants have found that post irradiation stability is achieved by using synthetic polymers rather than natural cellulose based polymers as paste stabilizing agents in the acidic aqueous paste. Without wishing to be tied to a theory, it is believed that the cellulose polymers are susceptible to degrade into low molecular weight species in acidic aqueous medium during terminal sterilization, thereby affecting the viscosity of the paste during storage. The preferred polymer based stabilizing agent for the acidic aqueous paste is polyvinyl pyrrolidone (PVP) and polyethylene glycol (PEG).

With respect to the alkaline non-aqueous paste, Applicants have found that the use of either the natural when preferentially used in combination of antioxidants or synthetic polymers does not affect the alkaline non-aqueous paste's long term storage stability even after it is exposed to the terminal sterilization process, such as gamma irradiation. The preferred paste stabilizing agent for the alkaline non-aqueous paste is polyethylene glycol (PEG), cellulose-based polymer, such as hydroxyethylcellulose (HEC) when preferentially using an antioxidant such as thioglycerol.

According to an aspect of the invention, the acidic aqueous paste composition comprises at least one acidic calcium phosphate mineral, at least one synthetic polymer based paste stabilizing agent, a pH buffering agent and a humectant.

The at least one acidic calcium phosphate mineral is preferably monocalcium phosphate monohydrate (MCPM), monocalcium phosphate anhydrous (MCPA), dicalcium phosphate dehydrate (DCPD), and dicalcium phosphate anhydrous (DCPA).

The at least one synthetic polymer-based paste stabilizing agent is, preferably, polyvinyl pyrrolidone (PVP) and polyethylene glycol (PEG).

The pH buffering agent is, preferably, citric acid, tartaric acid and malic acid and their salts, including trisodium citrate and disodium tartarate. The most preferred pH buffering agent is citric acid.

The humectant is, preferably, glycerol and propylene glycol.

In a preferred embodiment, the acidic paste composition comprises monocalcium phosphate monohydrate (MCPM) and dicalcium phosphate anhydrous (DCPA), citric acid, water, glycerol, PVP and PEG.

According to an aspect of the invention, the alkaline non-aqueous paste comprises at least one basic calcium phosphate mineral, at least one paste stabilizing agent, a surfactant and a solvent.

The at least one basic calcium phosphate mineral is, preferably, β-tricalcium phosphate, α-tricalcium phosphate, tetracalcium phosphate, oxyapatite, hydroxyapatite or calcium-deficient hydroxyapatite. The most preferred at least one basic calcium phosphate mineral is tetracalcium phosphate (TTCP).

The at least one stabilizing agent used in the alkaline non-aqueous pastes, is preferably either natural with or without an antioxidant or synthetic polymer based. Without wishing to be bound to a theory, it is believed that in a water-free paste system, both the natural and synthetic polymers survive; therefore, providing paste stability during terminal sterilization and storage. The preferred at least one stabilizing agent is polyethylene glycol (PEG), cellulose-based polymer, such as hydroxyethylcellulose (HEC) and the preferred at least one antioxidant for use with the cellulose based polymer is thioglycerol.

The surfactant is, preferably, glycerol monostearate, lecithin, phospholipids, glycerol distearate, polyethylene glycol distearate, block polymers of PEG-PPG-PEG or PPG-PEG-PPG, Tween, Span, any polysorbate fatty acid ester or sorbitol esters. The most preferred surfactant is polysorbate 80 (Tween 80).

The solvent is, preferably, one or more of the following; glycerol, thioglycerol, ethanol, propanol, and propylene glycol. The most preferred solvents glycerin and propylene glycol.

In a preferred embodiment, the alkaline non-aqueous paste comprises tetracalcium phosphate, polyethylene glycol, polysorbate 80, and propylene glycol.

In accordance with another aspect of the invention, the alkaline non-aqueous paste comprises a bimodal mean particle size distribution of at least one basic calcium phosphate mineral in order to maximize the paste stability and cement reactivity. More preferably, the alkaline non-aqueous paste with a bimodal mean particle size distribution of TTCP was demonstrated to produce a bone cement that is superior than when a single mode mean particle size distribution of TTCP in the alkaline non-aqueous paste, when mixed with the acidic aqueous paste.

One aspect of the present invention is a calcium phosphate composition produced by mixing the acidic aqueous paste and the alkaline non-aqueous paste of the present invention. In an embodiment, the calcium phosphate cement is rapid setting. In another embodiment, the calcium phosphate cement is injectable. In yet another embodiment, the calcium phosphate cement is rapid setting and injectable.

One aspect of the present invention is to ease the mixing and application of a CaPC in surgery. The approach taken here has been to completely eliminate the need for the three separate steps whereby the user must (i) mix the powder and liquid components to form a cement paste, (ii) transfer the cement paste into a delivery syringe and (iii) inject the cement paste into a bone cavity. Instead, the intention of this invention is to simplify by combining these three separate steps into one whereby the user is provided with a system that eliminates the need for transfer of the cement paste into a syringe system and concurrently and homogeneously mixes the components during the injection step.

Yet another aspect of the present invention is to a method of making a post irradiation shelf-stable dual paste direct injectable bone cement precursor compositions comprising mixing at least one synthetic polymer based paste stabilizing agent, a pH buffering agent, and water; adding at least one acidic calcium phosphate mineral to the mixture of the at least one synthetic polymer based paste stabilizing agent, the pH buffering agent and water to form an acidic aqueous paste; and mixing at least one paste stabilizing agent, a surfactant, and a solvent; adding at least one basic calcium phosphate mineral to the mixture of the at least one paste stabilizing agent, the surfactant, and the solvent to produce an alkaline non-aqueous paste.

In accordance with the invention, the method may further comprise a step of storing the acidic aqueous paste in a container; storing the alkaline non-aqueous paste in another container; and providing a device which would inject the pastes concurrently from the separate containers to a static mixing device so that said a blended paste of said acidic aqueous paste and said alkaline non-aqueous paste can inject to a site of application by the action of applied injection force.

One aspect of the invention is to provide a kit comprising a dual paste injectable cement precursor system comprising two holding chambers, wherein the first holding chamber comprises an acidic aqueous paste and the second holding chamber comprises an alkaline non-aqueous paste, and a mixing device where the acidic aqueous paste and the alkaline non-aqueous paste are mixed and injected to a site of application by the action of applied injection force.

Another aspect of the invention is to provide a device for a dual paste injectable bone cement precursor system comprising: a syringe body and a static mixing tip, wherein the syringe body comprises a first holding chamber containing an acidic aqueous paste comprising at least one acidic calcium phosphate mineral, at least one synthetic polymer-based paste stabilizing agent, a pH buffering agent and a humectant, and a second holding chamber containing an alkaline non-aqueous paste comprising at least one basic calcium phosphate mineral, at least one paste stabilizing agent, a surfactant and a solvent, and the static mixing tip comprises a structure which allows the two pastes to be blended and to be applied to a desired site. In one embodiment, a device is a dual barrel syringe system having a static mixer wherein the acidic aqueous paste of the present invention and the alkaline non-aqueous paste of the present invention are stored in a one to one ratio in each barrel, and be mixed in the static mixer to be blended and initiate setting and be applied to a desired site. In another embodiment, the device and/or the dual barrel syringe system maintains a seal to reduce moisture and air leaks to ensure shelf life protection.

DETAILED DESCRIPTION OF THE PREFERRED EMBODIMENTS

Figure 1:
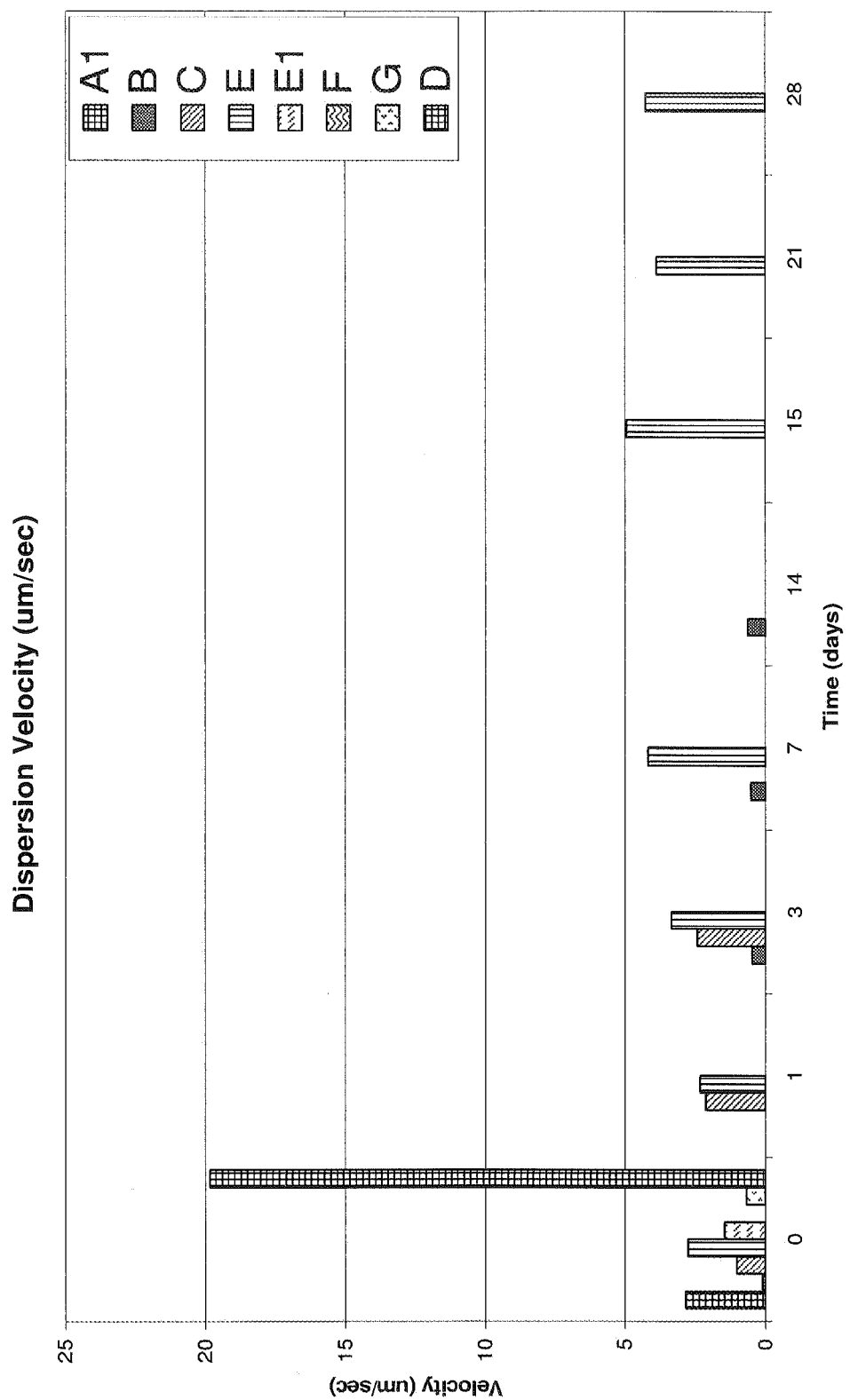
FIG. 1 is a graphical overview of the dispersion analysis results of the acidic aqueous pastes and alkaline non-aqueous pastes of the present invention.

Throughout the entire specification, including the claims, the word "comprise" and variations of the word, such as "comprising" and "comprises," as well as "have," having," "includes," "include," and "including," and variations thereof, means that the named steps, elements or materials to which it refers are essential, but other steps, elements, or materials may be added and still form a construct with the scope of the claim or disclosure. When recited in describing the invention and in a claim, it means that the invention and what is claimed is considered to what follows and potentially more. These terms, particularly when applied to claims, are inclusive or open-ended and do not exclude additional, unrecited elements or methods steps.

The term "cement" herein is used interchangeably with cement formulation, cement composition and bone cement.

The term "between" as used in connection with a range includes the endpoints unless the context suggests otherwise.

The term "long term shelf-life" or "shelf-stable" herein means that the cement precursors(s), such as calcium phosphate mineral(s), and other powder materials in a paste will not separate out from the liquid when exposed to real time and accelerated aging conditions and will set when mixed with the corresponding acidic aqueous/alkaline non-aqueous paste to form a bone cement after the dual paste system has been stored in a sealed container for a predetermined period of time, for at least 1.5 months, preferably 3 months, and more preferably for at least 6 months and most preferably more than 1 year according to the accelerated aging test described in details below.

The term "alkaline non-aqueous paste" as used in accordance with the present invention herein means that this paste includes a non-aqueous solvent such as glycerol or propylene glycol and a basic calcium phosphate mineral, and that the paste is able to be miscible with the acidic aqueous paste. It is contemplated that in an alkaline non-aqueous paste, there may be trace amounts of moisture present, such as moisture that is unavoidably present notwithstanding reasonably prudent steps to exclude such moisture. The alkaline non-aqueous paste itself is not a cement, in that the paste itself does not set to form a hard material in ordinary use. Rather, when the alkaline non-aqueous is combined with the acid aqueous paste, a cement is formed thereby.

The term "acidic aqueous paste" as used in accordance with the present invention herein means that this paste includes water and an acidic calcium phosphate mineral, and that the paste is able to be miscible with the alkaline non-aqueous paste. The acidic aqueous paste itself is not a cement, in that the paste itself does not set to form a hard material in ordinary use. Rather, when the acidic aqueous paste is combined with the alkaline non-aqueous paste, a cement is formed thereby.

The term "injectable" as used in accordance with the present invention herein means that the acidic aqueous paste which is held in one container, and the alkaline non-aqueous paste which is held in a separate container may be delivered to the site of application through a cannula, a needle, a catheter, a syringe or a specially designed static mixing device by the action of an applied injection force. This injection force is tested at an ambient temperature of between 18° C. to 22° C. as set out in Examples 1, 2 and 3 below, and does not exceed 225 N, and more preferably 150 N to allow ease of injectability for the end user.

The term "rapid setting" as used in accordance with the present invention herein means that when the acidic aqueous paste and the alkaline non-aqueous paste are mixed and delivered to a defect site, the mixture forms a cement in about 10 minutes or less, preferably in about 9 minutes or less, most preferably in about 8 minutes or less when the defect temperature is about 32° C.

The term "set" as used in accordance with the present invention herein means that the penetration force measured according to the wet field penetration resistance test described in details below is preferably greater than 10 MPa, more preferably greater than 20 MPa and most preferably greater than 24 MPa.

The term "biocompatible" when used in conjunction with a cement contemplates a cement that is not rejected by soft tissue or hard tissue when used in vivo in the intended application.

Kit

Preferably, the system is provided in the form of a kit, the kit including the dual paste injectable cement precursor system comprising an acidic aqueous paste and an alkaline non-aqueous paste in separate moisture impermeable holding chambers (e.g. glass, cyclic olefin copolymer plastic, etc) throughout the products shelf life and an appropriate mixing device. The mixing device may be conventional, or may otherwise be a device suitable for use in conjunction with the cement precursor systems taught in the art.

Preferably, a device having a syringe body with a static mixing tip, the mixing tip comprising an auger-like structure that allows the two pastes to be blended rapidly and subsequently to be applied to the desired area is used in accordance with the invention. The syringe body may include a region that serves as the container for separate pastes, by providing separate holding chambers for the acidic aqueous paste and the alkaline non-aqueous paste.

Any suitable container may be used in conjunction with the invention, and thus, for instance, the container may be any appropriate box, or bag, or package.

Cement Precursors in the Pastes

The cement precursors may be any material suitable for use in forming a biocompatible cement. Numerous cement chemistries may be used in conjunction with the invention. In a preferred embodiment, a calcium phosphate cement is employed. In one embodiment, a calcium phosphates cement may be formed by combining at least one calcium phosphate material in at least one of the two precursor pastes. In another embodiment, a calcium phosphate cement, for example, hydroxyapatite, is formed by combining at least two dissimilar calcium phosphate materials present respectively in the two precursor pastes.

The pastes need not include only a single calcium phosphate material, and thus, for instance, the pastes each may include multiple calcium phosphate materials, and some of the third calcium phosphate material may be present initially in either or both of the pastes.

Generally, it is preferred that the Ca/P ratio ranges from 0.5 to 2.0 in each paste. In some embodiments, particularly when it is desired to form hydroxyapatite, one of the pastes includes a calcium phosphate in which the Ca/P ratio is less than 5/3, and the other includes a calcium phosphate compound in which the Ca/P ratio is greater than 5/3. The Ca/P ratio in hydroxyapatite is 5/3, and it is believed that providing calcium and phosphate in both greater and lesser amounts will drive formation of hydroxyapatite. It is not necessary to employ two such pastes, especially if a setting accelerator is used. In some embodiments, the Ca/P ratio in one of the pastes is equal to 5/3. In the formation of hydroxyapatite with the heretofore described calcium phosphate cements, the formation of hydroxyapatite can proceed slowly if the cement is initially formed at a pH above about 8, and if the selection of precursors for such a cement would provide a pH of 8 or above, use of a setting accelerator is preferred. In some embodiments, one may choose the overall Ca/P in order to cause formation of a different calcium phosphate in the resulting cement, such as DCPA or DCPD.

Furthermore, the particle size of the at least one calcium phosphate can be adjusted to modify the rate of the rapid dissolution of calcium phosphate minerals during cement mixing and injection, as the particle size has effects on the chemistry of the setting reactions by controlling the pH and consequently, the setting reaction rate and strength.

The particle size of the calcium phosphate minerals (as well as any other powder components added to each paste) was measured using Beckman Coulter's LS 13320 Series particle size analyzer. It is noted that the particle size values mentioned herein refer to Volume Mean Diameter values.

A sample for analysis was prepared by adding a small amount of powder in a carrier medium. When the powder material is calcium phosphate, ethanol was used. The slurry was mixed aggressively for a short period of time prior to the analysis of the sample.

Volume distributions of mean diameter values were then obtained. Upon measurement completion, the cell was emptied and cleaned and refilled with the slurry of the powder in a carrier medium and repeated several times.

Calcium Phosphate Minerals

That at least one source of calcium phosphate useful in accordance with the present invention generally includes numerous calcium phosphate minerals already known in the art, such as those taught by Brown and Chow in U.S. Reissue Pats. 33,161 and 33,221, Chow and Takagi in U.S. Pat. Nos. 5,522,893, 5,542,973, 5,545,254, 5,525,148, 5,695,729 and 6,325,992 and by Constantz in U.S. Pat. Nos. 4,880,610 and 5,047,031, teachings of which are incorporated herein by reference.

Any suitable calcium compound may be used in conjunction with this embodiment of the invention. In preferred embodiments, the calcium compound is a calcium phosphate having a Ca/P ratio ranging from about 0.5-2.0. Alternatively, or in addition thereto, the calcium compound may be a suitable calcium salt, or any suitable calcium compound that is sparing soluble in acid.

Exemplary calcium compounds suitable for use in conjunction with the invention include tetracalcium phosphate (TTCP), dicalcium phosphate anhydrous (DCPA), dicalcium phosphate dihydrate (DCPD), monocalcium phosphate anhydrous (MCPA), monocalcium phosphate monohydrate (MCPM), alpha-tricalcium phosphate (alpha-TCP), beta tricalcium phosphate (beta-TCP), hydroxyapatite (HA), amorphous calcium phosphate (ACP), octacalcium phosphate (OCP), calcium deficient hydroxyapatite (CDH), carbonate-containing hydroxyapatite (CHA), fluoride-containing hydroxyapatite (FHA), calcium lactate, calcium sulfate, calcium gluconate, calcium lactate gluconate, calcium glycerophosphate, calcium silicate, calcium hydroxide, and other biocompatible calcium compounds with a solubility of at least about 2 wt. % in the acid environment. Generally, calcium compounds that are biocompatible and that form a suitable cement may be used. The selection of a particular calcium compound may be based on numerous factors, including for instance the reactivity of the compound with the selected acid, and also the overall acid and base contents of the cement, and the desired end cement products Acidic Aqueous Paste In a preferred embodiment, the acidic aqueous paste composition comprises at least one acidic calcium phosphate mineral, at least one synthetic polymer based paste stabilizing agent, a pH buffering agent, a humectant, and water.

Acidic Calcium Phosphate Mineral

The acidic calcium phosphate mineral is preferably monocalcium phosphate monohydrate (MCPM), monocalcium phosphate anhydrous (MCPA), dicalcium phosphate dehydrate (DCPD), and dicalcium phosphate anhydrous (DCPA).

In a preferred embodiment, the mean particle size of the at least one acidic calcium phosphate mineral is between about 0.4 µm to about 200 µm, preferably about 0.7 µm to about 150 µm, and most preferably about 1 µm to about 90 µm.

In a more preferred embodiment wherein the acidic aqueous paste contains MCPM and DCPA, the mean particle size of MCPM is between about 0.4 µm to about 200 µm, preferably about 10 µm to about 150 µm, and most preferably about 30 µm to about 90 µm; the mean particle size of the DCPA is between about 0.4 µm to about 200 µm, preferably about 0.7 µm to about 50 µm, and most preferably about 1 µm to about 20 µm.

With respect to an amount of the acidic calcium phosphate mineral present in the acidic aqueous paste, it may be present in an amount of between about 1% w/w and about 80% w/w, and preferably about 5% w/w and about 65% w/w based on the total weight of the acidic aqueous paste.

In a preferred embodiment wherein the acidic aqueous paste contains MCPM and DCPA, MCPM may be present in an amount of between about 1% w/w and about 40% w/w, more preferably between about 5% w/w and about 20% w/w based on the total weight of the acidic aqueous paste; and DCPA may be present in an amount of between about 20% w/w and about 80% w/w, more preferably between about 40% w/w and about 65% w/w based on the total weight of the acidic aqueous paste.

Synthetic Polymer Based Paste Stabilizing Agent for the Acidic Aqueous Paste

The synthetic paste stabilizing agent in accordance with the present invention can be any material useful for stabilizing the acidic aqueous paste to prevent or retard an unwanted alteration of the physical state, such as separation of the powder components from the liquid components even after the paste is exposed to gamma radiation for terminal sterilization.

Applicants have found that post irradiation stability of the acidic aqueous paste is achieved by using synthetic polymer based paste stabilizing agent rather than natural cellulose based polymer. Without wishing to be tied to a theory, it is believed that the natural cellulose polymers are susceptible to degrade into low molecular weight species in acidic aqueous medium during terminal sterilization, thereby affecting the viscosity of the paste during storage.

The synthetic polymer based paste stabilizing agent in accordance with the present invention allows the acidic aqueous paste to stay storage stable for a long term, even after it is exposed to gamma radiation for sterilization.

Examples of a paste stabilizing agent which can be used in the acidic aqueous paste, without limitation, are PVP and PEG.

Although PVP is quite often cross linked in a basic medium during terminal sterilization, in an acidic medium, it is believed that the rate of cross linking is slow, especially in the presence of calcium salts as the pyrrolidone ring is primarily engaged with calcium salts through ionic interactions. Accordingly, the pyrrolidone ring is protected from not being opened and cross-linked. Although an acidic aqueous paste comprising a higher amount of PVP provides greater stability, this results in the reduction of the reactivity to the alkaline non-aqueous paste. Therefore, when PVP is used as a synthetic polymer based paste stabilizing agent for the acidic aqueous paste, it must be present in an optimal level.

The mean molecular weight (Mw) of the PVP in the acidic aqueous paste is between about 1,000 Mw to about 1,000,000 Mw, preferably between about 10,000 Mw to about 100,000 Mw, more preferably about 20,000 to about 80,000 Mw, even more preferably about between 40,000 Mw to about 70,000 Mw, but most preferably between 50,000 Mw to about 60,000.

With respect to the amount of the PVP in the acidic aqueous paste, the PVP may be present in an amount of between about 0% w/w and about 40% w/w, more preferably between about 0.05% w/w and about 20% w/w, but most preferably between 1% w/w to 10% w/w based on the total weight of the paste.

It is also believed that PEG bonds with hydrogen molecule in the acidic aqueous paste, thereby slowing down the mobility of water molecules in the system to produce stability. The molecular weight of the PEG chain is important as rigidity of the chain itself plays important role in stability. Although an acidic aqueous paste comprising a higher amount of PEG provides greater stability; this results in the reduction of the reactivity to the alkaline non-aqueous paste. Therefore, when PEG is used as a synthetic polymer based paste stabilizing agent for the acidic aqueous paste, it must be present in an optimal level.

The mean molecular weight (Mw) of the PEG in the acidic aqueous paste is between about 1,000 Mw to about 60,000 Mw, preferably between about 5,000 Mw to about 40,000 Mw, more preferably between about 10,000 Mw to about 40,000 Mw, but most preferably between 15,000 Mw to about 25,000 Mw.

With respect to the amount of the PEG in the acidic aqueous paste, the PEG may be present in an amount of between about 0% w/w and about 40% w/w, more preferably between about 0.05% w/w and about 20% w/w, but most preferably between 1% w/w to 10% w/w based on the total weight of the paste.

pH Buffering Agent

In the acidic aqueous paste, a pH buffering agent is added to the paste in order to provide lower pH as well as to form ionic interaction with at least one acidic calcium minerals to provide paste stability. Without wishing to be bound to a theory, it is also believed that the pH buffering agent in accordance with the present invention can act as a setting accelerating agent, influencing the setting reaction once the acidic aqueous paste and the alkaline non-aqueous paste systems are combined.

Examples of a pH buffering agent which can be used in the present invention, without limitation, are citric acid, phosphoric acid, tartaric acid and malic acid and their salts, including trisodium citrate, sodium phosphate monobasic and disodium tartarate. The preferred pH buffering agent is citric acid. The citric acid can come in several forms, which are anhydrous, monohydrate, or dihydrate. The preferred form of citric acid is the monohydrate form.

The pH buffering agent is present in an amount of between about 1% w/w to about 10% w/w, or more preferably, in an amount of between about 5% w/w to about 8% w/w.

Humectant

The humectant in accordance with the present invention can be any material to help the water molecules within the acidic aqueous paste intact through formation of hydrogen bonds, thus enhancing the paste stability and injectability of the paste. Although an acidic aqueous paste comprising a higher amount of humectant provides greater injectability, this results in the reduction of the reactivity to the alkaline non-aqueous paste. Therefore, when a humectant is used in the acidic aqueous paste, it must be present in an optimal level.

Examples of a humectant which can be used in the present invention, without limitation, are glycerol, propylene glycol, glycol triacetate, sorbitol, lactic acid, and urea. The most preferred humectant is glycerol.

With respect to the amount of the humectant, it may be present in the acidic aqueous paste in an amount of between about 0% w/w and about 4% w/w, more preferably between about 0.5% w/w and about 2% w/w based on the total weight of the acidic aqueous paste.

Water

The amount of water present in the acidic aqueous paste may be between about 10 w/w % and about 30 w/w %, more preferably between about 15 w/w % and about 25 w/w %, based on the total weight of the aqueous paste.

Alkaline Non-Aqueous Paste

In a preferred embodiment, the alkaline non-aqueous paste composition comprises at least one basic calcium phosphate mineral, at least one paste stabilizing agent, a surfactant, and solvent.

Basic Calcium Phosphate Mineral

The basic calcium phosphate mineral is, preferably, β-tricalcium phosphate, α-tricalcium phosphate, tetracalcium phosphate, oxyapatite, hydroxyapatite or calcium-deficient hydroxyapatite. The most preferred at least one basic calcium phosphate mineral is tetracalcium phosphate (TTCP).

In another preferred embodiment, the mean particle size of at least one basic calcium phosphate mineral is between about 0.4 μm to about 200 μm, preferably between 2 μm to about 90 μm, and more preferably 30 μm to about 70 μm, and most preferably 45 μm to about 55 μm.

In another embodiment wherein the alkaline non-aqueous paste contains bimodal distribution of TTCP, the mean particle size of the first set of TTCP is preferably between 2 μm to about 60 μm, more preferably between 10 μm to 30 μm, and the mean particle size of the second set of TTCP is between 10 μm to 90 μm, more preferably between 25 μm to 60 μm.

With respect to an amount of the basic calcium phosphate mineral present in the alkaline non-aqueous paste, it may be present in an amount of between about 1% w/w and about 90% w/w, and preferably about 10% w/w and about 80% w/w based on the total weight of the alkaline non-aqueous paste.

In the most preferred embodiment wherein the alkaline non-aqueous paste contains TTCP, the TTCP may be present in an amount of between about 40% w/w and about 90% w/w, more preferably between about 60% w/w and about 80% w/w based on the total weight of the alkaline non-aqueous paste.

Paste Stabilizing Agent for the Alkaline Non-Aqueous Paste

The paste stabilizing agent in accordance with the present invention can be any material useful for stabilizing the alkaline non-aqueous paste to prevent or retard an unwanted alteration of the physical state, such as separation of the powder components from the liquid components even after the paste is exposed to gamma radiation for terminal sterilization.

With respect to the alkaline non-aqueous paste, Applicants have surprisingly found that the use of either the natural or synthetic polymers does not affect the non-aqueous paste's long term storage stability even after it is exposed to the terminal sterilization process, such as gamma irradiation.

Without wishing to be bound by a theory, it is believed that when a paste stabilizing agent, such as PEG and/or cellulose polymers are dissolved in non-aqueous solvents such as glycerol or propylene glycol, a complex hydrogen bond network is formed in which the TTCP particles are suspended, thereby making the paste storage stable for a long term.

Examples of a paste stabilizing agent which can be used in the alkaline non-aqueous paste, without limitation, synthetic polymer such as PEG or a natural cellulose-based polymer, such as hydroxyethylcellulose (HEC), ethylcellulose, methylcellulose, hydroxypropyl cellulose, carboxymethyl cellulose, hydroxypropyl methyl cellulose. The most preferred paste stabilizing agent for the alkaline non-aqueous paste is PEG and HEC when preferentially using an antioxidant such as thioglycerol.

The mean molecular weight (Mw) of the PEG in the alkaline non-aqueous paste is between about 1,000 Mw to about 60,000 Mw, preferably between about 5,000 Mw to about 40,000 Mw, more preferably between about 10,000 Mw to about 40,000 Mw, but most preferably between 15,000 Mw to about 25,000 Mw.

With respect to the amount of the PEG in the alkaline non-aqueous paste, the PEG may be present in an amount of between about 0% w/w and about 20% w/w, more preferably between about 0.5% w/w and about 10% w/w, but most preferably between 1% w/w to 5% w/w based on the total weight of the paste.

The mean molecular weight (Mw) of the HEC in the alkaline non-aqueous paste is between about 90,000 Mw to about 1,500,000 Mw, preferably between about 1,000,000 Mw to about 1,400,000 Mw.

With respect to the amount of the HEC present in the alkaline non-aqueous paste, the HEC may be present in an amount of between about 0% w/w and about 5% w/w, more preferably between about 0% w/w and about 1% w/w, but most preferably 0% w/w to 0.5% w/w based on the total weight of the paste.

Surfactant

The surfactant in accordance with the present invention can be any material useful for preventing coagulation of colloidal particles by helping particles suspend in liquid and to reduce the surface tension of the basic calcium phosphate mineral in the alkaline non-aqueous paste.

The surfactant of the present invention may be supplied in only the one of the at least two pastes, or in some or all of the at least two pastes. However, in a preferred embodiment where there are two pastes in a system containing acidic aqueous paste and alkaline non-aqueous paste, the surfactant is in the alkaline non-aqueous paste only.

Examples of a surfactant which can be used in the present invention, without limitation, are glycerol monostearate, lecithin, phospholipids, glycerol distearate, polyethylene glycol distearate, block polymers of PEG-PPG-PEG or PPG-PEG-PPG, Tween, Span, any polysorbate fatty acid ester or polysorbate monooleate (from oleic acid) or sorbitol esters. The most preferred surfactant is polysorbate 80.

With respect to the amount of the surfactant, it may be present in an amount of between about 0% w/w and about 4% w/w, more preferably between about 0.5% w/w and about 2% w/w based on the total weight of the total formulation when at least two pastes are combined.

In a preferred embodiment of the present invention, the surfactant may be present in an amount of between about 0% w/w and about 4% w/w, more preferably between about 0.5% w/w and about 2% w/w based on the total weight of the acidic aqueous paste containing MCPM and DCPA; and the reaction retarding agent may be present in an amount of between about 0% w/w and about 4% w/w, more preferably between about 0.5% w/w and about 2% w/w based on the total weight of the alkaline non-aqueous paste containing TTCP.

Solvent in Alkaline Non-Aqueous Paste

The solvent for the alkaline non-aqueous paste can be any suitable non-aqueous liquid at room temperature, which excludes water. Examples of the solvent for the alkaline non-aqueous paste in accordance with the present invention, without limitation, are glycerol, ethanol, propanol, and propylene glycol. The preferred solvent is glycerin and propylene glycol due to their biocompatibility and complete miscibility with water.

The non-aqueous liquid solvent in the alkaline non-aqueous paste may be present in an amount of between about 10 w/w % and about 40 w/w %, more preferably between about 20 w/w % and about 30 w/w %, and most preferably between about 22 w/w % and about 28 w/w %, based on the total weight of the alkaline non-aqueous paste.

Additive(s)

Various additives may be included in the inventive cements, slurries and pastes to adjust their properties and the properties of the hydroxyapatite products made from them. For example, proteins, osteoinductive and/or osteoconductive materials, X-ray opacifying agents, medicaments, supporting or strengthening filler materials, crystal growth adjusters, viscosity modifiers, pore forming agents, and other additives and a mixture thereof may be incorporated without departing from the scope of this invention.

The nature of the compounds and functional materials present in the cements is not limited to the heretofore described ingredients, but to the contrary any other suitable osteoconductive, bioactive, bioinert, or other functional materials may be used in conjunction with the invention. When used, these optional ingredients may be present in any amounts suitable for their intended purposes. For instance, particularly in the case of the calcium phosphate cements, one or both cement precursor phases may include a setting accelerator, such as phosphoric acid, hydrochloric acid, sulfuric acid, oxalic acid, and salts thereof, and sodium phosphate, potassium phosphate, and sodium fluoride. In some embodiments, some of the calcium phosphate materials themselves may promote setting; for instance, MCPM and certain nano-sized calcium phosphate materials may promote setting of the cement. Any other suitable setting accelerator may be used in conjunction with the present invention. Setting accelerators are described in more detail in Chow et al., U.S. Patent Application Publication No. 2005/0074415, published Apr. 7, 2005.

In some embodiments, one of the cement precursors includes an osteoinductive protein, by which is contemplated any protein that is useful in assisting in or inducing bone formation. Osteoinductive proteins are deemed particularly suitable for use in conjunction with the carboxyl/calcium cement systems because, at least for many known osteoinductive proteins, such proteins may denature at an alkaline pH.

Another optional ingredient is a filler, such as a radiopaque filler. The radio opaque filler may, for instance, be a suitable bismuth, barium, or iodide compound, such as barium sulfate or bismuth hydroxide. Other suitable fillers include bioglass, silica based, alumina based, biphasic calcium phosphate, calcium silicate, calcium sulfate, granular calcium phosphate ceramics, and the like.

A medicament, such as zinc, magnesium, strontium, boron, copper, silica or any other suitable medicament may be included in one or both of the phases of the cement precursors. Either or both of the phases may include a material that is intended to affect the viscosity, cohesiveness, or injectability of the phases. Any suitable biocompatible ingredient.

In some embodiments, a macropore forming material may be used. As disclosed, for instance, in prior U.S. Pat. Nos. 7,018,460 and 6,955,716, a macropore forming material, such as mannitol, is useful in forming a macropores, or pores having a size greater than 150 microns. Such pores are sometimes deemed desirable and that they create a structure that may be useful in promoting growth of soft tissue in or near the region of these cements.

Also as described in U.S. Pat. Nos. 7,018,460 and 6,955,716, in some embodiments, one or more strength-enhancing components, such as fibers, meshes, or the like, may be used. Such components may be resorbable or non-resorbable.

EXAMPLES

Several formulations in accordance with the present invention were made as illustrated below in Examples 1, 2 and 3. A table of abbreviations used in Examples 1, 2 and 3 is provided below.

| Abbreviations |
| --- |
| PEG = Polyethylene Glycol |
| MCPM = Monocalcium Phosphate Monohydrate |
| DCPA = Dicalcium phosphate Anhydrous |
| TTCP = Tetracalcium Phosphate |
| CAM = Citric Acid Monohydrate |
| SPM = Sodium Phosphate Monobasic |
| Span 80 = Sorbitan Monooleate |
| Tween 80 = Polysorbate 80 |
| HEC = Hydroxyethylcellulose |
| TSCD = Trisodium Citrate Dihydrate |

Example 1

| Paste Type | Material | % w/w | Mean Particle Size (μm)/Mean Molecular Weight (Mw) |
| --- | --- | --- | --- |
| Acidic Aqueous Paste | MCPM | 11.60 | 40-60 μm |
| | DCPA | 58.04 | 1-12 μm |
| | Water (WFI) | 18.59 | |
| | Citric Acid Monohydrate | 7.45 | |
| | PEG | 1.21 | 20k Mw |
| | Glycerol | 1.33 | |
| | PVP | 1.78 | 58k Mw |
| | TOTAL | 100.00 | |
| Alkaline Non-aqueous Paste | TTCP | 57.63 | 10-30 μm |
| | TTCP | 14.12 | 30-80 μm |
| | Propylene Glycol | 24.86 | |
| | Tween 80 | 1.13 | |
| | PEG | 2.26 | 20k Mw |
| | TOTAL | 100.00 | |

Example 2

Examples of Various Acidic Aqueous Pastes

| Formulation Family Reference | Material | Paste Weights (grams) | Mean Particle size (μm)/Mean Molecular weight (Mw) |
| --- | --- | --- | --- |
| A | MCPM | 10.28 | 40-60 μm |
| | DCPA | 51.42 | 1-12 μm |
| | Water | 17.38 | |
| | TSCD | 0.95 | 150-220 μm |
| | CAM | 6.96 | |
| | Glycerol | 0.36 | |
| | PEG | 0.93 | 20K Mw |
| B | MCPM | 10.00 | 40-60 μm |
| | DCPA | 50.00 | 1-12 μm |
| | Glycerol | 0.36 | |
| | SPM | 0.5 | |
| | Water | 15.02 | |
| | CAM | 6.01 | |
| | PEG | 1.43 | 20k Mw |
| | PVP | 3.47 | 58k Mw |
| C | MCPM | 10.00 | 40-60 μm |
| | DCPA | 50.00 | 1-12 μm |
| | Glycerol | 1.2 | |
| | SPM | 25.0 | |
| | Water | 16.01 | |
| | CAM | 6.41 | |
| | PEG | 1.66 | 20k Mw |
| | PVP | 2.25 | 58k Mw |

-continued

| Formulation Family Reference | Material | Paste Weights (grams) | Mean Particle size (μm)/Mean Molecular weight (Mw) |
|---|---|---|---|
| D | MCPM | 10.0 | 40-60 μm |
|  | DCPA | 50.0 | 1-12 μm |
|  | Water | 19.45 |  |
|  | CAM | 7.87 |  |
|  | HEC | 0.28 | 1.3 × 10^6 Mw |
| E | MCPM | 11.60 | 40-60 μm |
|  | DCPA | 58.04 | 1-12 μm |
|  | Water (WFI) | 18.59 |  |
|  | CAM | 7.45 |  |
|  | PEG | 1.21 | 20k Mw |
|  | Glycerol | 1.33 |  |
|  | PVP | 1.78 | 58k Mw |
| F | MCPM | 10.0 | 40-60 μm |
|  | DCPA HS II | 54.98 | 1-12 μm |
|  | SPM | 0.5 |  |
|  | Water | 40.0 |  |
|  | CAM | 14 |  |
| G | MCPM | 10.0 | 40-60 μm |
|  | DCPA HS II | 50.0 | 1-12 μm |
|  | Phosphoric Acid | 0.5 | 85% |
|  | Water | 100.0 |  |
|  | CAM | 40.04 |  |
|  | PVP C30 | 14.0 |  |

Example 3

Examples of Various Alkaline Non-Aqueous Pastes

| Formulation Family Reference | Material | Paste Weights (grams) | Mean Particle size/ Mean Molecular weight (Mw) |
|---|---|---|---|
| A1 | TTCP | 48.0 | 10-30 μm |
|  | TTCP | 12.0 | 30-80 μm |
|  | Propylene Glycol | 20.93 |  |
|  | Span 80 | 0.92 |  |
|  | PEG | 1.84 | 20k Mw |
| B1 | TTCP | 48.0 | 10-30 μm |
|  | TTCP | 12.0 | 30-80 μm |
|  | Propylene Glycol | 20.93 |  |
|  | Tween 80 | 0.92 |  |
|  | PEG | 1.84 | 20k Mw |
| C1 | TTCP | 60.0 | 10-30 μm |
|  | Propylene Glycol | 22.67 |  |
|  | HEC | 0.33 | 1.3 × 10^6 Mw |
| D1 | TTCP | 57.63 | 10-30 μm |
|  | TTCP | 14.12 | 30-80 μm |
|  | Propylene Glycol | 24.86 |  |
|  | Tween 80 | 1.13 |  |
|  | PEG | 2.26 | 20k Mw |
| E1 | TTCP | 48.0 | 10-30 μm |
|  | TTCP | 12.0 | 30-80 μm |
|  | Glycerol | 9.0 |  |
|  | PEG | 10.0 | 20k Mw |
|  | Triacetin | 90.0 |  |

The dual pastes containing precursor for bone cement of the present invention were subjected to an array of qualification tests to verify that they meet the performance requirements. The dual pastes system of the present invention was analyzed for long term stability.

Long term stability may be measured by any technique or using any criteria deemed appropriate. In accordance with one such technique, a sample of the material or materials constituting the paste is first gamma irradiated and put in a accelerated aging chamber which is heated to a temperature of 40° C. at a relative humidity of 75%, and held at this temperature for a set period of time. The acidic aqueous paste and the alkaline non-aqueous paste then are mixed to form a cement, and the setting time of the cement is evaluated as compared with the original setting time of a similar cement made without thermal treatment of either of the pastes. If the setting time of the cement made with the thermally treated phase is approximately equal to the setting time of the similar cement, the paste may be deemed suitably stable for use in conjunction with the present invention. The invention is not limited to cement precursor systems that meet this criterion; rather, the foregoing is provided to illustrate one of but many possible methods for evaluating stability.

In the present case, the pastes illustrated in Examples 1, 2 and 3 were first sterilized using gamma radiation and put in an accelerated aging test chamber. Subsequently, the acidic aqueous paste and the alkaline non-aqueous paste were mixed to form a bone cement and the resulting bone cement was tested for (1) aging stability, (2) wet field penetration resistance, (3) compression strength and (4) injectability, which are described in more details below.

Gamma Irradiation

Irradiation dose ranging between 25-35 kGy was used to sterilize the pastes of Examples 1, 2 and 3 following the protocol of ISO 11137-2, disclosure of which is incorporated by reference herein. The irradiation dose mentioned above is merely a preferred range, and that the irradiation dose should not be limited to the range mentioned above, but should be selected such that it is sufficient to sterilize while the adverse effects such as degradation, loss of stability, loss of efficacy of the pastes, etc. are minimal.

After the exposure to gamma irradiation for sterilization, the pastes were tested both pre-aged and post-aged after being put in the accelerated aging test conditions for a predetermined period of time as explained below.

Aging Test

The aqueous and alkaline non-aqueous pastes as described in Examples 1, 2 and 3 above were analyzed for long-term stability.

The various pastes were packaged in an air and moisture impermeable double barreled syringe system and were placed in a climatic oven set at an ambient temperature of 21° C. and aged for a set period of time.

After the exposure in the aging test conditions for a predetermined period of time, the pastes were analyzed to assess the dual pastes' stability and cement performance. A successful outcome in terms of paste stability was considered achieved when the aged paste test results were directly comparable with the non-aged, i.e. control samples, which were tested at a timepoint of zero. Such a result indicated no detectable degradation of the paste system over time under the test conditions used. The results are presented in Table A below.

Dispersion Analysis; LUMiSizer Testing

The cements were produced as described in Examples 1, 2 and 3, were exposed to gamma radiation for sterilization and were tested for stability via dispersion analysis by use of LUMiSizer analysis. Approximately 0.5 ml of the paste to be tested was filled into a clean LUMiSizer vial to the predefined line on the vial. The vial was then sealed with the supplied screw cap lid and this sealed vial was then placed into the LUMiSizer and secured. The dispersion analysis test can now be performed and run to completion. The output from this test method displays the dispersion of the paste system in relation to time over a specific gravity applied onto the paste via centrifugal force. This dispersion data can be used to indirectly correlate the stability of the paste system and used for comparative purposes between various paste systems. A successful outcome in terms of paste stability was considered to be achieved when the aged paste dispersion test results were directly comparable with the non-aged, i.e. control samples, which were tested at a timepoint of zero. Such a result indicated no detectable degradation of the paste system over time under the test conditions used. FIG. 1 is an overview to dispersion analysis results generated for various formulations that were tested at various time points (0, 1, 3, 7, 14, 15, 21 and/or 28 days respectively).

Wet Field Penetration Resistance Test

Figure 2:
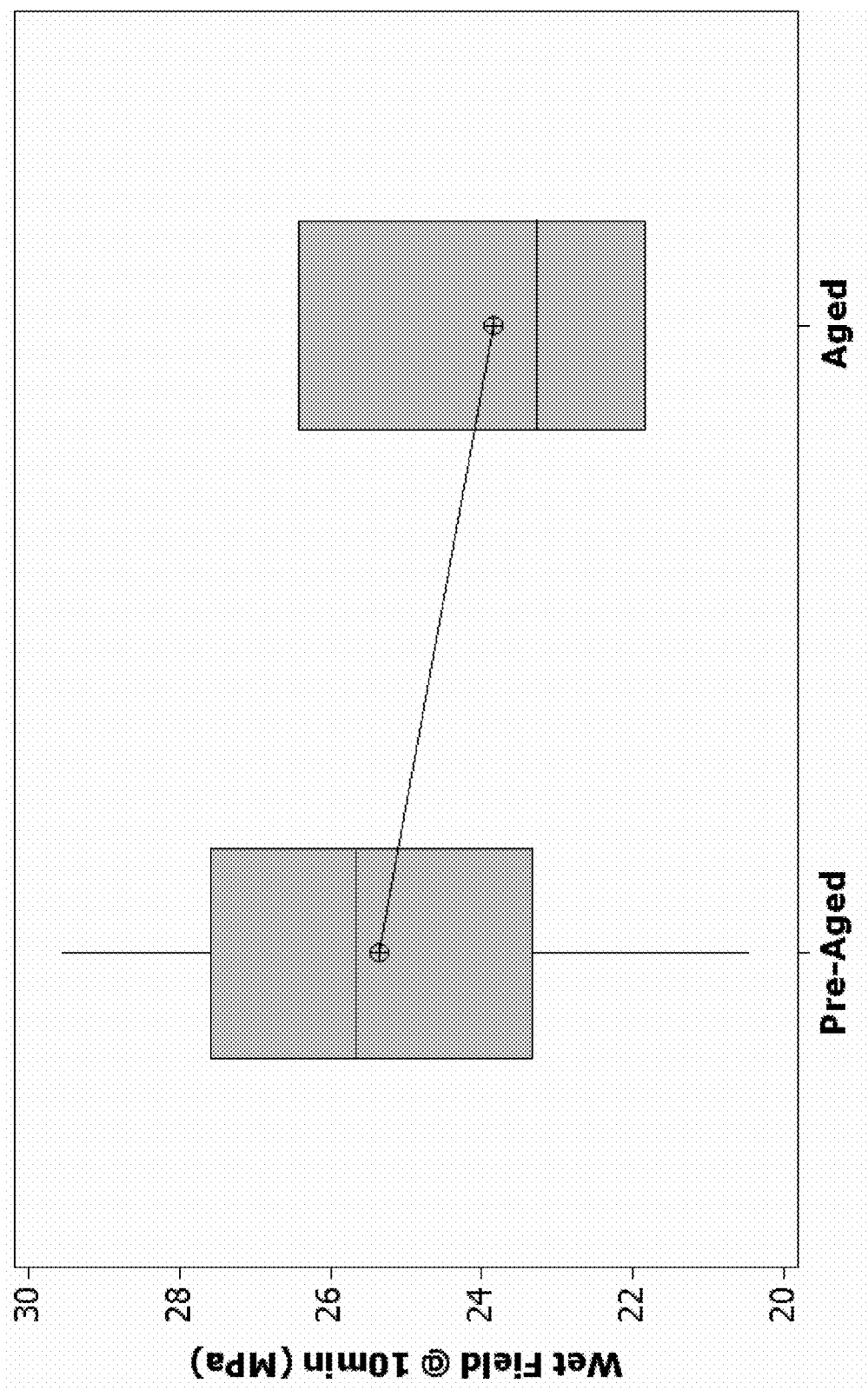
FIG. 2 is a graphical overview of the analysis results of wet field tests of the formulation of the present invention comprising the acidic aqueous paste E of Example 2 and the alkaline non-aqueous paste D1 of Example 3 before and after the aging test.

The cements produced as described in Examples 1, 2 and 3, which were exposed to gamma radiation for sterilization and the accelerated aging conditions, were tested for wet field penetration resistance. The test consists of applying a load applicator through the cement at specific time points. The load applicator was made up of a small cylindrical stainless steel needle with 1/16" in diameter. Immediately after initial mixing of the acidic aqueous paste and alkaline non-aqueous paste, the cement composition was deposited into a long groove (1/4" wide×1/4" deep) of a block heated at 32° C. One minute after the initial mixing, the cement was subjected to a constant flow of saturated phosphate solution using a Watson Marlow 323 peristaltic pump set at 20 rpm. The solution was kept constant at 32° C. Ten minutes after the initial mixing, the load applicator was made to penetrate the cement for 1.27 mm and the result force was recorded. Table A below shows the results of the penetration resistance tests using the bone cements produced according to Examples 1, 2 and 3. FIG. 2 is a graphical overview of the analysis results of wet field tests of the formulation of the present invention comprising the acidic aqueous paste E of Example 2 and the alkaline non-aqueous paste D1 of Example 3 before and after the aging test. This wet field penetration resistance test result can be considered having a successful outcome in terms of demonstrating paste stability as can be seen from this figure that the aged paste penetration test results were directly comparable with the non-aged, i.e. control samples, which were tested at a timepoint of zero with no statistically significant difference shown (p>0.05). Such a result indicates no detectable degradation of the paste system over time under the test conditions used.

TABLE A

| Formulations | | Test Method | | |
|---|---|---|---|---|
| Acidic Aqueous | Alkaline Non-Aqueous | Wet Field (MPa) | Inject-ability (N) | Compression @ 4 hr post mixing (MPa) |
| D PRE-AGED | C1 PRE-AGED | 28.1 | 25.0 | 7.2 |
| D Aged | C1 Aged | 39.0 | 50.0 | 7.08 |
| A PRE-AGED | C1 PRE-AGED | 31.74 | 86.5 | 6.03 |
| A Aged | C1 Aged | 28.65 | 77.7 | 6.65 |
| B PRE-AGED | C1 PRE-AGED | 24.85 | 99.0 | 4.0 |
| B Aged | C1 Aged | 22.78 | 111.0 | 4.03 |
| C PRE-AGED | A1 PRE-AGED | 27.12 | 60.5 | 5.54 |
| C Aged | A1 Aged | 19.43 | 65.5 | 5.51 |
| C PRE-AGED | B1 PRE-AGED | 23.59 | 66.9 | 5.74 |
| C Aged | B1 Aged | 17.01 | 65.9 | 5.79 |
| E PRE-AGED | D1 PRE-AGED | 25.36 | 88.72 | |
| E Aged | D1 Aged | 23.85 | 82.03 | |

Injectability Test

The cements produced as described in Examples 1, 2 and 3, which were exposed to gamma radiation for sterilization and the accelerated aging conditions, were also tested for injectability. A dual barrel syringe containing the combination of paste systems as described in Table above are placed in a test rig in a Tinius Olsen Tensometer electro-mechanical testing machine. The start of the test is T=0. Once the plunger reaches the set preload (5N), it displaces at a rate of 25 mm/min until the required extension is reached (15 mm). Once the 20 seconds wait has elapsed, the test resumes until a total displacement of 30 mm is reached unless a maximum load of 300N is reached first. This 'stop-start' function is required to provide the user with a flexibility in usage of the dual paste system with an injectability window.

Figure 3:
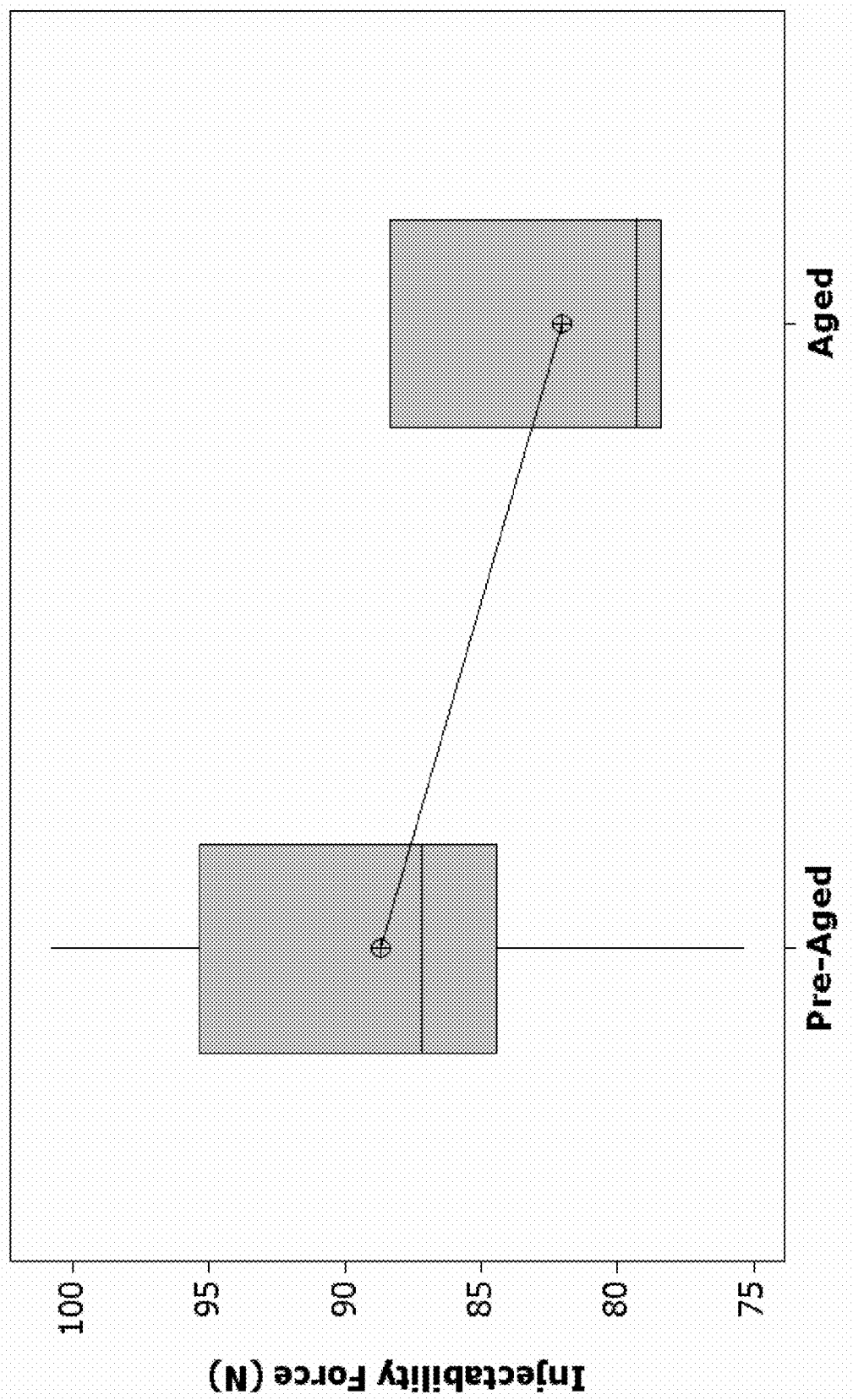
FIG. 3 is a graphical overview of the analysis results of injectability tests of the formulation of the present invention comprising the acidic aqueous paste E of Example 2 and the alkaline non-aqueous paste D1 of Example 3 before and after the aging test.

For this test, maximum initial injectability force shall not exceed 225N, more preferably 150N for both the initial injectability as well as re-starting after stopping injection for 20 sec. The results are recorded in the Table A above. FIG. 3 is a graphical overview of the analysis results of wet injectability tests of the formulation of the present invention comprising the acidic aqueous paste E of Example 2 and the alkaline non-aqueous paste D1 of Example 3 before and after the aging test. This test result can be considered having a successful outcome in terms of demonstrating paste stability as can be seen from this figure that the aged paste injectability test results were directly comparable with the non-aged, i.e. control samples, which were tested at a timepoint of zero. Such a result indicates no detectable degradation of the paste system over time under the test conditions used. The injection force to enable the evaluation of ease of injectability can be obtained from ANSI/AAMI HE75:2009 (p. 367, FIG. 22.13) whereby 95% of males and 50% of females can squeeze up to 107N over a grip span range from 4.5 cm to 11 cm.

Compression Test

The cements produced as described in Examples 1, 2 and 3 were also tested for compressive strength. A set amount of the dual paste system (as listed in Table A) is injected into a cylindrical mould to form a set cement shape of diameter 6 mm and 12 mm length. The mould is then placed in Phosphate Buffered Saline (PBS) solution and the cement is allowed to set in this mould. Remove the set cement at a 4 hrs time point after incubation in PBS.

Measure the diameter and length of each specimen before separately placing each sample to be tested on the Tinius Olsen Tensometer electro-mechanical testing machine, ensuring that the load rate is set at 1 mm/min. Record the maximum load at which the cylindrical sample fails under compressive loading. The results are recorded in the Table A above.

The invention claimed is:

1. A bone cement precursor system comprising:
   a first container containing an acidic aqueous paste comprising monocalcium phosphate monohydrate (MCPM) and dicalcium phosphate anhydrous (DCPA), citric acid, water, glycerol, polyvinyl pyrrolidone (PVP) and polyethylene glycol (PEG), and
   a second container containing an alkaline non-aqueous paste comprising at least one basic calcium phosphate mineral, at least one paste stabilizing agent, a surfactant and a solvent.

2. The bone cement precursor system of claim 1, wherein the mean particle size of said monocalcium phosphate monohydrate (MCPM) and dicalcium phosphate anhydrous (DCPA) is between about 1 μm to about 90 μm.

3. The bone cement precursor system of claim 1, wherein the amount of said monocalcium phosphate monohydrate (MCPM) and dicalcium phosphate anhydrous (DCPA) present in said acidic aqueous paste is between about 5% w/w to about 65% w/w based on the total weight of said acidic aqueous paste.

4. The bone cement precursor system of claim 2, wherein the mean particle size of said monocalcium phosphate monohydrate (MCPM) is about 30 μm to about 90 μm.

5. The bone cement precursor system of claim 2, wherein the mean particle size of said dicalcium phosphate anhydrous (DCPA) is about 1 μm to about 20 μm.

6. The bone cement precursor system of claim 1, wherein the amount of said polyvinyl pyrrolidone (PVP) and polyethylene glycol (PEG) is 1% w/w and about 10% w/w based on the total weight of said acidic aqueous paste.

7. The bone cement precursor system of claim 1, wherein the amount of said citric acid present in said acidic aqueous paste is between about 5% w/w and about 8% w/w based on the total weight of said acidic aqueous paste.

8. The bone cement precursor system of claim 1, wherein the amount of said glycerol present in said acidic aqueous paste is between about 0.5% w/w and about 2% w/w based on the total weight of said acidic aqueous paste.

9. The bone cement precursor system of claim 1, wherein the amount of said water present in said acidic aqueous paste is between about 15 w/w % to about 25 w/w % based on the total weight of said acidic aqueous paste.

10. The bone cement precursor system of claim 1, wherein said system further comprises an additive.

11. The bone cement precursor system of claim 10, wherein said additive is selected from the group consisting of a protein, osteoinductive material, osteoconductive material, x-ray opacifying agent, medicament, supporting or strengthening filler material, crystal growth adjuster, viscosity modifier, pore forming agent, radiopaque filler and mixtures thereof.

12. A calcium phosphate composition produced by mixing said acidic aqueous paste and said alkaline non-aqueous paste of claim 1.

13. The bone cement precursor system of claim 1, wherein the mean molecular weight (Mw) of PEG in the acidic aqueous paste is between about 1,000 Mw to about 60,000 Mw.

14. The bone cement precursor system of claim 1, wherein the mean molecular weight (Mw) of PVP in the acidic aqueous paste is between about 10,000 Mw to about 100,000 Mw.

15. A bone cement precursor system comprising:
a first container containing an acidic aqueous paste comprising at least one acidic calcium phosphate mineral, at least one synthetic polymer-based paste stabilizing agent, a pH buffering agent and a humectant, and
a second container containing an alkaline non-aqueous paste comprising tetracalcium phosphate (TTCP), polyethylene glycol (PEG), polysorbate 80, and propylene glycol.

16. The bone cement precursor system of claim 15, wherein the mean particle size of TTCP is between about 10 μm to about 60 μm.

17. The bone cement precursor system of claim 15, wherein the amount of TTCP in said alkaline non-aqueous paste is between about 10 w/w % to about 80 w/w % based on the total weight of said alkaline non-aqueous paste.

18. The bone cement precursor system of claim 15, wherein said alkaline non-aqueous paste comprises a bimodal mean particle size distribution of the TTCP.

19. The bone cement precursor system of claim 15, wherein the amount of the PEG present in said alkaline non-aqueous paste is between about 1 w/w % to about 5 w/w % based on the total weight of said alkaline non-aqueous paste.

20. The bone cement precursor system of claim 15, wherein the amount of the polysorbate 80 in said alkaline non-aqueous paste is between about 0.5 w/w % to about 2 w/w % based on the total weight of said alkaline non-aqueous paste.

21. The bone cement precursor system of claim 15, wherein the amount of said propylene glycol in said alkaline non-aqueous paste is between about 22 w/w % to about 28 w/w % based on the total weight of said alkaline non-aqueous paste.

22. The bone cement precursor system of claim 15, wherein said system further comprises an additive.

23. The bone cement precursor system of claim 22, wherein said additive is selected from the group consisting of a protein, osteoinductive material, osteoconductive material, x-ray opacifying agent, medicament, supporting or strengthening filler material, crystal growth adjuster, viscosity modifier, pore forming agent, radiopaque filler and mixtures thereof.

24. A calcium phosphate composition produced by mixing said acidic aqueous paste and said alkaline non-aqueous paste of claim 15.

25. The bone cement precursor system of claim 15, wherein the at least one synthetic polymer-based paste stabilizing agent is polyvinyl pyrrolidone (PVP) and polyethylene glycol (PEG).

26. The bone cement precursor system of claim 25, wherein the mean molecular weight (Mw) of PEG in the acidic aqueous paste is between about 1,000 Mw to about 60,000 Mw.

27. The bone cement precursor system of claim 25, wherein the mean molecular weight (Mw) of PVP in the acidic aqueous paste is between about 10,000 Mw to about 100,000 Mw.

* * * * *